United States Patent
Udagawa et al.

(10) Patent No.: US 9,657,300 B2
(45) Date of Patent: May 23, 2017

(54) POLYNUCLEOTIDES HAVING LEADER SEQUENCE FUNCTION

(71) Applicant: NOVOZYMES A/S, Bagsvaerd (DK)

(72) Inventors: Hiroaki Udagawa, Chiba (JP); Rikako Taira, Chiba (JP); Shinobu Takagi, Chiba (JP)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 14/947,014

(22) Filed: Nov. 20, 2015

(65) Prior Publication Data

US 2016/0068847 A1    Mar. 10, 2016

Related U.S. Application Data

(63) Continuation of application No. 13/704,856, filed as application No. PCT/EP2011/060532 on Jun. 23, 2011, now Pat. No. 9,222,095.

(60) Provisional application No. 61/359,167, filed on Jun. 28, 2010.

(30) Foreign Application Priority Data

Jun. 25, 2010    (EP) .................... 10167301

(51) Int. Cl.
*C12N 15/80*    (2006.01)
*C07K 14/195*    (2006.01)

(52) U.S. Cl.
CPC ............ *C12N 15/80* (2013.01); *C07K 14/195* (2013.01)

(58) Field of Classification Search
None
See application file for complete search history.

(56) References Cited

FOREIGN PATENT DOCUMENTS

JP    2004275177 A    10/2004

OTHER PUBLICATIONS

Innis et al., Science, 1985, vol. 228, pp. 21-26.*
Database EMBL [Online], Jan. 28, 2007 (Jan. 28, 2007), "Aspergillus niger conti g Anl5c0240, complete genome." XP002595911 retrieved from EBI accession No. EMBLAM270351, Database accession No. AM270351.*
Gomi et al., Agric. Biol. Chem., 1987, vol. 51, pp. 2549-2555.*
Database EMBL [Online], Jan. 28, 2007 (Jan. 28, 2007), "Aspergillus niger conti g Anl5c0240, complete genome." XP002595911 retrieved from EBI accession No. EMBL:AM270351, Database accession No. AM270351.
Database EMBL [Online], Jul. 16, 2005 (Jul. 16, 2005), "Asn_03019 Aspergillus niger pBluescript (EcoRI-Xhol) Aspergillus niger cDNA clone Asn_03019, mRNA sequence." XP002595909 retrieved from EBI accession No. EMBL:DR703311, Database accession No. DR703311.
Semova et al, "Generation, annotation, and analysis of an extensive Aspergillus niger EST collection," BMC Microbiology, 2006, vol. 6, pp. 1-10.
Brandhorst et al, "Effects of leader sequences upon the heterologous expression of restictocin in Aspergillus nidulans and Aspergillus niger," Can. J. Microbiol., 1995, vol. 41, No. 7, pp. 601-611.
Calos 1978, "DNA sequence for a low-level promoter of the lac repressor gene and an 'up' promoter mutation", Nature 1978, vol. 274, pp. 762-765.
Jobling et al. "Enhanced translation of chimaeric messenger RNAs containing a plant viral untranslated leader sequence", Nature 1987, vol. 35, No. 12, pp. 622-625.
Innis et al., Expression, Glycosylation, and Secretion of an Aspergillus Glucoamylase by Saccharomyces cerevisiae, Science 1985, vol. 222, pp. 21-26.

* cited by examiner

*Primary Examiner* — Mindy G Brown
(74) *Attorney, Agent, or Firm* — Robert Starnes

(57) ABSTRACT

The present invention relates to isolated polynucleotides having leader sequence function. The invention also relates to nucleic acid constructs, vectors, and host cells comprising the polynucleotides as well as methods using the polynucleotides for production of polypeptides.

14 Claims, No Drawings

SEQUENCE LISTING

```
<160> NUMBER OF SEQ ID NOS: 50

<210> SEQ ID NO 1
<211> LENGTH: 88
<212> TYPE: DNA
<213> ORGANISM: Aspergillus niger

<400> SEQUENCE: 1
caacaatctc agaacaccaa tatcaattca tctcgagtct gaactcagac aacacaaatt      60
cttcaaaatt gaggatttag tcttgatc                                        88

<210> SEQ ID NO 2
<211> LENGTH: 88
<212> TYPE: DNA
<213> ORGANISM: Aspergillus niger

<400> SEQUENCE: 2
caacaatctc agaacagcga tatcaattca tctcgagtct gaacccaaac aacaaaatcc      60
cttcagaatt gaggatttag ttttgatc                                        88

<210> SEQ ID NO 3
<211> LENGTH: 30
<212> TYPE: DNA
<213> ORGANISM: Artificial
<220> FEATURE:
<223> OTHER INFORMATION: Primer TCGA-F

<400> SEQUENCE: 3
tgggggatcc accatgcgtt tcacgctcct                                      30

<210> SEQ ID NO 4
<211> LENGTH: 33
<212> TYPE: DNA
<213> ORGANISM: Artificial
<220> FEATURE:
<223> OTHER INFORMATION: Primer TCGA-R

<400> SEQUENCE: 4
ctcgagttaa ttaactaccg ccaggtgtcg ttc                                  33

<210> SEQ ID NO 5
<211> LENGTH: 36
<212> TYPE: DNA
<213> ORGANISM: Artificial
<220> FEATURE:
<223> OTHER INFORMATION: Primer nidP-f

<400> SEQUENCE: 5
tttgctagca ctagttacta aatgacgttt gtgaac                               36

<210> SEQ ID NO 6
<211> LENGTH: 31
<212> TYPE: DNA
<213> ORGANISM: Artificial
<220> FEATURE:
<223> OTHER INFORMATION: Primer nidP-r

<400> SEQUENCE: 6
ttgcatgctc tagaggagcg aaccaattct c                                    31

<210> SEQ ID NO 7
<211> LENGTH: 28
<212> TYPE: DNA
<213> ORGANISM: Artificial
```

```
<220> FEATURE:
<223> OTHER INFORMATION: Primer nidPT-f

<400> SEQUENCE: 7
tttactagta cgagaaaaga gttggact                                          28

<210> SEQ ID NO 8
<211> LENGTH: 29
<212> TYPE: DNA
<213> ORGANISM: Artificial
<220> FEATURE:
<223> OTHER INFORMATION: Primer nidPT-r

<400> SEQUENCE: 8
tttctagagc gaaccaattc tctcccagc                                         29

<210> SEQ ID NO 9
<211> LENGTH: 28
<212> TYPE: DNA
<213> ORGANISM: Artificial
<220> FEATURE:
<223> OTHER INFORMATION: Primer 5NA1F

<400> SEQUENCE: 9
gtttaaacct atctgttccc tccccccc                                          28

<210> SEQ ID NO 10
<211> LENGTH: 38
<212> TYPE: DNA
<213> ORGANISM: Artificial
<220> FEATURE:
<223> OTHER INFORMATION: Primer 5NA1R

<400> SEQUENCE: 10
tttactagtg ctagctgact tctatataaa aatgagta                               38

<210> SEQ ID NO 11
<211> LENGTH: 30
<212> TYPE: DNA
<213> ORGANISM: Artificial
<220> FEATURE:
<223> OTHER INFORMATION: Primer 3NA1F

<400> SEQUENCE: 11
tttctagagt atatgatggt actgctattc                                        30

<210> SEQ ID NO 12
<211> LENGTH: 32
<212> TYPE: DNA
<213> ORGANISM: Artificial
<220> FEATURE:
<223> OTHER INFORMATION: Primer 3NA1R

<400> SEQUENCE: 12
gcggccgcgc attctcctag ttactgatga ct                                     32

<210> SEQ ID NO 13
<211> LENGTH: 32
<212> TYPE: DNA
<213> ORGANISM: Artificial
<220> FEATURE:
<223> OTHER INFORMATION: Primer p384

<400> SEQUENCE: 13
aagtcagcta gccgtcggtg tgatggaaat cc                                     32
```

```
<210> SEQ ID NO 14
<211> LENGTH: 48
<212> TYPE: DNA
<213> ORGANISM: Artificial
<220> FEATURE:
<223> OTHER INFORMATION: Primer p385

<400> SEQUENCE: 14
tcaaaattga ggatttagtc ttgatcggat ctccaccatg aagttctt         48

<210> SEQ ID NO 15
<211> LENGTH: 29
<212> TYPE: DNA
<213> ORGANISM: Artificial
<220> FEATURE:
<223> OTHER INFORMATION: Primer p386

<400> SEQUENCE: 15
acccggatct taattaacta ctctgtgac                              29

<210> SEQ ID NO 16
<211> LENGTH: 48
<212> TYPE: DNA
<213> ORGANISM: Artificial
<220> FEATURE:
<223> OTHER INFORMATION: Primer p387

<400> SEQUENCE: 16
aagaacttca tggtggagat ccgatcaaga ctaaatcctc aattttga         48

<210> SEQ ID NO 17
<211> LENGTH: 23
<212> TYPE: DNA
<213> ORGANISM: Artificial
<220> FEATURE:
<223> OTHER INFORMATION: Primer p264

<400> SEQUENCE: 17
ttcgctagca tggtgttttg atc                                    23

<210> SEQ ID NO 18
<211> LENGTH: 118
<212> TYPE: DNA
<213> ORGANISM: Artificial
<220> FEATURE:
<223> OTHER INFORMATION: Primer p310

<400> SEQUENCE: 18
tggtggatcc gatcaagact aaatcctcaa ttttgaagaa tttgtgttgt ctgagttcag    60
actcgagatg aattgatatt ggtgttctga gattgttgct ccaagcatgg catccctt    118

<210> SEQ ID NO 19
<211> LENGTH: 28
<212> TYPE: DNA
<213> ORGANISM: Artificial
<220> FEATURE:
<223> OTHER INFORMATION: Primer p262

<400> SEQUENCE: 19
tcggctagca tggtgttttg atcattttt                              28

<210> SEQ ID NO 20
<211> LENGTH: 28
<212> TYPE: DNA
<213> ORGANISM: Artificial
```

-continued

```
<220> FEATURE:
<223> OTHER INFORMATION: Primer p263

<400> SEQUENCE: 20
cgggatcccc cagttgtgta tatagagg                                    28

<210> SEQ ID NO 21
<211> LENGTH: 23
<212> TYPE: DNA
<213> ORGANISM: Artificial
<220> FEATURE:
<223> OTHER INFORMATION: Primer p264

<400> SEQUENCE: 21
ttcgctagca tggtgttttg atc                                         23

<210> SEQ ID NO 22
<211> LENGTH: 117
<212> TYPE: DNA
<213> ORGANISM: Artificial
<220> FEATURE:
<223> OTHER INFORMATION: Primer p270

<400> SEQUENCE: 22
ggtggatccg atcaaaacta atcctcaat tctgaaggga ttttgttgtt tgggttcaga    60
ctcgagatga attgatatcg ctgttctgag attgttgctc caagcatggc atccctt     117

<210> SEQ ID NO 23
<211> LENGTH: 20
<212> TYPE: DNA
<213> ORGANISM: Artificial
<220> FEATURE:
<223> OTHER INFORMATION: Primer

<400> SEQUENCE: 23
aatccggatc ctttcctata                                             20

<210> SEQ ID NO 24
<211> LENGTH: 20
<212> TYPE: DNA
<213> ORGANISM: Artificial
<220> FEATURE:
<223> OTHER INFORMATION: Primer

<400> SEQUENCE: 24
gatggagcgc gcctagaagc                                             20

<210> SEQ ID NO 25
<211> LENGTH: 20
<212> TYPE: DNA
<213> ORGANISM: Artificial
<220> FEATURE:
<223> OTHER INFORMATION: Primer

<400> SEQUENCE: 25
ttcaccacca tcctcagcac                                             20

<210> SEQ ID NO 26
<211> LENGTH: 20
<212> TYPE: DNA
<213> ORGANISM: Artificial
<220> FEATURE:
<223> OTHER INFORMATION: Primer

<400> SEQUENCE: 26
```
tcttgacctg caaagtgttg                                          20

<210> SEQ ID NO 27
<211> LENGTH: 29
<212> TYPE: DNA
<213> ORGANISM: Artificial
<220> FEATURE:
<223> OTHER INFORMATION: Primer ppyrG F

<400> SEQUENCE: 27
acttctagaa tagcgacaag ccgaacggc                                29

<210> SEQ ID NO 28
<211> LENGTH: 42
<212> TYPE: DNA
<213> ORGANISM: Artificial
<220> FEATURE:
<223> OTHER INFORMATION: Primer ppyrG R

<400> SEQUENCE: 28
taccgccagg tgtcagtcac cctcaaagtc caactctttt ct                 42

<210> SEQ ID NO 29
<211> LENGTH: 42
<212> TYPE: DNA
<213> ORGANISM: Artificial
<220> FEATURE:
<223> OTHER INFORMATION: Primer pTamg F

<400> SEQUENCE: 29
agaaaagagt tggactttga gggtgactga cacctggcgg ta                 42

<210> SEQ ID NO 30
<211> LENGTH: 90
<212> TYPE: DNA
<213> ORGANISM: Artificial
<220> FEATURE:
<223> OTHER INFORMATION: Primer pTamg R

<400> SEQUENCE: 30
gcttgcatgc actagctagt tgaagttcct atactatttg aagaatagga actcggaata    60
ggaacttcaa cctagaggag agagttgaac                                     90

<210> SEQ ID NO 31
<211> LENGTH: 47
<212> TYPE: DNA
<213> ORGANISM: Artificial
<220> FEATURE:
<223> OTHER INFORMATION: Primer pTer F

<400> SEQUENCE: 31
gtccaggttc aactctctcc actagcaaag tattttcggt acgattt             47

<210> SEQ ID NO 32
<211> LENGTH: 90
<212> TYPE: DNA
<213> ORGANISM: Artificial
<220> FEATURE:
<223> OTHER INFORMATION: Primer pTer R

<400> SEQUENCE: 32
gcttgcatgc actagctagt tgaagttcct atactatttg aagaatagga actcggaata    60
ggaacttcaa cctagaggag agagttgaac                                     90

```
<210> SEQ ID NO 33
<211> LENGTH: 42
<212> TYPE: DNA
<213> ORGANISM: Artificial
<220> FEATURE:
<223> OTHER INFORMATION: Primer pTniaD F

<400> SEQUENCE: 33
agaaaagagt tggactttga gggtgactga cacctggcgg ta                     42

<210> SEQ ID NO 34
<211> LENGTH: 51
<212> TYPE: DNA
<213> ORGANISM: Artificial
<220> FEATURE:
<223> OTHER INFORMATION: Primer pTniaD R

<400> SEQUENCE: 34
ctcctacatc aaccgccgca tctgagtcga gattatccaa gggaatgact t           51

<210> SEQ ID NO 35
<211> LENGTH: 51
<212> TYPE: DNA
<213> ORGANISM: Artificial
<220> FEATURE:
<223> OTHER INFORMATION: Primer pFLP F

<400> SEQUENCE: 35
taagtcattc ccttggataa tctcgactca gatgcggcgg ttgatgtagg a           51

<210> SEQ ID NO 36
<211> LENGTH: 53
<212> TYPE: DNA
<213> ORGANISM: Artificial
<220> FEATURE:
<223> OTHER INFORMATION: Primer pFLP R

<400> SEQUENCE: 36
ccaacaaccc aactgacagg ggatcgatcc accatgcccc agttcgatat cct         53

<210> SEQ ID NO 37
<211> LENGTH: 53
<212> TYPE: DNA
<213> ORGANISM: Artificial
<220> FEATURE:
<223> OTHER INFORMATION: Primer ppxy F

<400> SEQUENCE: 37
aggatatcga actggggcat ggtggatcga tcccctgtca gttgggttgt tgg         53

<210> SEQ ID NO 38
<211> LENGTH: 30
<212> TYPE: DNA
<213> ORGANISM: Artificial
<220> FEATURE:
<223> OTHER INFORMATION: Primer ppxy R

<400> SEQUENCE: 38
ggatggatcc ggaagtgcgt tgatcattat                                   30

<210> SEQ ID NO 39
<211> LENGTH: 180
<212> TYPE: DNA
<213> ORGANISM: Artificial
<220> FEATURE:
<223> OTHER INFORMATION: Primer pFRT F
```

<400> SEQUENCE: 39

```
ttttttacgta aatatcagcc ctaacgtaat cggtaagcga gttgcccgcg caagcgagtt    60
gcccaccacc cgccatataa aaatttaaaa tgatcaaaac accatgctag cgaagttcct   120
atactttcta gagaatagga actcggaata ggaacttcaa gatgaattcg cggccgcggc   180
```

<210> SEQ ID NO 40
<211> LENGTH: 30
<212> TYPE: DNA
<213> ORGANISM: Artificial
<220> FEATURE:
<223> OTHER INFORMATION: Primer pFRT R

<400> SEQUENCE: 40

```
gcaccatatg cggtgtgaaa taccgcacag                                      30
```

<210> SEQ ID NO 41
<211> LENGTH: 29
<212> TYPE: DNA
<213> ORGANISM: Artificial
<220> FEATURE:
<223> OTHER INFORMATION: Primer pNA2F

<400> SEQUENCE: 41

```
cttcgctagc atggtgtttt gatcattt                                        29
```

<210> SEQ ID NO 42
<211> LENGTH: 118
<212> TYPE: DNA
<213> ORGANISM: Artificial
<220> FEATURE:
<223> OTHER INFORMATION: Primer pb-pas(J)R

<400> SEQUENCE: 42

```
tggtggatcc gatcaaaact aaatcctcaa ttctgaaggg attttgttgt ttgggttcag    60
actcgagatg aattgatatc gctgttctga gattgttgct ccaagcatgg catcccctt   118
```

<210> SEQ ID NO 43
<211> LENGTH: 119
<212> TYPE: DNA
<213> ORGANISM: Artificial
<220> FEATURE:
<223> OTHER INFORMATION: Primer pb-pas(D)R

<400> SEQUENCE: 43

```
atggtggatc cgatcaagac taaatcctca attttgaaga atttgtgttg tctgagttca    60
gactcgagat gaattgatat tggtgttctg agattgttgc tccaagcatg gcatcccctt  119
```

<210> SEQ ID NO 44
<211> LENGTH: 20
<212> TYPE: DNA
<213> ORGANISM: Artificial
<220> FEATURE:
<223> OTHER INFORMATION: Primer

<400> SEQUENCE: 44

```
tgattgcaag tccgagcaca                                                 20
```

<210> SEQ ID NO 45
<211> LENGTH: 20
<212> TYPE: DNA
<213> ORGANISM: Artificial
<220> FEATURE:
<223> OTHER INFORMATION: Primer

```
<400> SEQUENCE: 45
gaggtttgtc cgatgcgatt                                               20

<210> SEQ ID NO 46
<211> LENGTH: 28
<212> TYPE: DNA
<213> ORGANISM: Artificial
<220> FEATURE:
<223> OTHER INFORMATION: Primer pHiTe08 F

<400> SEQUENCE: 46
ctagctagcc gtcggtgtga tggaaatc                                      28

<210> SEQ ID NO 47
<211> LENGTH: 29
<212> TYPE: DNA
<213> ORGANISM: Artificial
<220> FEATURE:
<223> OTHER INFORMATION: Primer pHiTe08 R

<400> SEQUENCE: 47
cgcggatccg aagggaaggg gggaagttg                                     29

<210> SEQ ID NO 48
<211> LENGTH: 24
<212> TYPE: DNA
<213> ORGANISM: Artificial
<220> FEATURE:
<223> OTHER INFORMATION: Primer p354

<400> SEQUENCE: 48
ttcgctagcc gtcggtgtga tgga                                          24

<210> SEQ ID NO 49
<211> LENGTH: 117
<212> TYPE: DNA
<213> ORGANISM: Artificial
<220> FEATURE:
<223> OTHER INFORMATION: Primer p355

<400> SEQUENCE: 49
ggtggatccg atcaagacta aatcctcaat tttgaagaat ttgtgttgtc tgagttcaga   60
ctcgagatga attgatattg gtgttctgag attgttgaag atgaggcaat tggagca     117

<210> SEQ ID NO 50
<211> LENGTH: 118
<212> TYPE: DNA
<213> ORGANISM: Artificial
<220> FEATURE:
<223> OTHER INFORMATION: Primer p361

<400> SEQUENCE: 50
ggtggatccg atcaaaacta aatcctcaat tctgaaggga ttttgttgtt tgggttcaga   60
ctcgagatga attgatatcg ctgttctgag attgttgaag atgaggcaat tggagcag    118
```

US 9,657,300 B2

POLYNUCLEOTIDES HAVING LEADER SEQUENCE FUNCTION

CROSS-REFERENCE TO RELATED APPLICATIONS

This application is a continuation of U.S. application Ser. No. 13/704,856 filed Jun. 23, 2011, now U.S. Pat. No. 9,222,095, which is a 35 U.S.C. §371 national application of PCT/EP2011/060532 filed Jun. 23, 2011, which claims priority or the benefit under 35 U.S.C. §119 of European application no. 10167301.0 filed Jun. 25, 2010 and U.S. provisional application No. 61/359,167 filed Jun. 28, 2010, the contents of which are fully incorporated herein by reference.

REFERENCE TO A SEQUENCE LISTING

This application contains a Sequence Listing in computer readable form. The computer readable form is incorporated herein by reference.

BACKGROUND OF THE INVENTION

Field of the Invention

The present invention relates to polynucleotides having leader sequence function. In particular the invention relates to polynucleotides having leader sequence function in fungal host cells. The invention also relates to nucleic acid constructs, vectors, and host cells comprising the polynucleotides as well as methods of producing polypeptides using the polynucleotides of the invention.

Background of the Invention

The recombinant production of a heterologous protein in a fungal host cell, particularly a filamentous fungal cell such as *Aspergillus*, may provide for a more desirable vehicle for producing the protein in commercially relevant quantities.

Recombinant production of a heterologous protein is generally accomplished by constructing an expression cassette in which the DNA coding for the protein is placed under the expression control of a promoter, excised from a regulated gene, suitable for the host cell. The expression cassette is introduced into the host cell. Production of the heterologous protein is then achieved by culturing the transformed host cell under inducing conditions necessary for the proper functioning of the promoter contained on the expression cassette.

Improvement of the recombinant production of proteins generally requires the availability of new regulatory sequences which are suitable for controlling the expression of the proteins in a host cell. The regulatory sequence could be a suitable leader sequence, which is a nontranslated region of an mRNA that is important for translation by the host cell. The leader sequence is operably linked to the 5' terminus of the nucleotide sequence encoding the polypeptide.

Well known leaders for filamentous fungal host cells have previously been obtained from e.g. the genes for *Aspergillus oryzae* TAKA amylase and *Aspergillus nidulans* triose phosphate isomerase.

It is an object of the present invention to provide new leader sequences for use in fungal host cells and further provide improved methods for producing a polypeptide in a fungal host cell using the new leader sequences.

SUMMARY OF THE INVENTION

In a first aspect the invention relates to an isolated polynucleotide having leader sequence functionality, selected from the group consisting of:

(a) a polynucleotide comprising a nucleotide sequence having preferably at least 60%, more preferably at least 65%, more preferably at least 70%, more preferably at least 75%, more preferably at least 80%, more preferably at least 85%, even more preferably at least 90%, and most preferably at least 95% sequence identity to SEQ ID NO: 1 or 2;

(b) a polynucleotide that hybridizes under preferably at least medium-high stringency conditions, most preferably at least high stringency, and even most preferably at least very high stringency conditions with the polynucleotide of SEQ ID NO: 1 or 2;

(c) a variant comprising a substitution, deletion, and/or insertion of one or more (several) nucleotides of SEQ ID NO: 1 or 2.

The invention further relates to nucleic acid constructs, such as expression vectors and plasmids, and host cells comprising the isolated polynucleotide of the first aspect of the invention. Finally, the invention related to methods for producing polypeptides using a polynucleotide of the invention.

DEFINITIONS

Sequence Identity: The relatedness between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Subsequence: The term "subsequence" is defined herein as a nucleotide sequence having one or more (several) nucleotides deleted from the 5' and/or 3' end of the sequence of SEQ ID NO: 1 or SEQ ID NO:2; or a homologous sequence thereof; wherein the subsequence has the ability to function as a leader sequence. In a preferred aspect, a subsequence contains at least 10 nucleotides, more preferably at least 25 nucleotides, and even more preferred at least 50 nucleotides and most preferred at least 75 nucleotides of the sequence of SEQ ID NO: 1 or SEQ ID NO:2 or a homologous sequence thereof.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the function of the polynucleotide) or may give rise to an altered function of the polynucleotide. An allelic variant of a polynucleotide having leader sequence function is a polynucleotide having leader sequence function derived from an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide in a method of the present invention. Each control sequence may be native or foreign to the polynucleotide sequence or native or foreign to each other. Such control sequences include, but are not limited to, a polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with a coding region of a nucleotide sequence encoding a polypeptide.

Promoter: The term "promoter" is defined herein as a nucleotide sequence that is recognized by a host cell for expression of a polynucleotide sequence operably linked with the promoter. The promoter sequence contains transcriptional control sequences that mediate the transcription of the polynucleotide sequence. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell. Promoters have a complex block-modular structure and contain numerous short functional elements such as a transcription factor binding site, a RNA polymerase recognition site, an mRNA initiation site. These sequences have no exact uniform location and are dispersed in the 5'-flanking region up to about 1 kb upstream of the mRNA initiation site where transcription starts.

Operably linked: The term "operably linked" denotes herein a configuration in which a control sequence is placed at an appropriate position relative to the coding sequence of a polynucleotide sequence such that the control sequence directs the expression of the coding sequence of a polypeptide.

Expression: The term "expression" includes any step involved in the production of a polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

DETAILED DESCRIPTION OF THE INVENTION

Leader Sequence or 5' Untranslated Region (5' UTR)

Leader sequences are normally understood as a nontranslated region of an mRNA, meaning that it is transcribed but not translated. The corresponding DNA sequence is located between the promoter and the coding sequence of a gene, and the leader is important for translation by the host cell. The leader sequence is operably linked to the 5' terminus of the nucleotide sequence encoding the polypeptide. A promoter sequence is a nucleotide sequence that is recognized by a host cell for expression of a polynucleotide encoding a polypeptide. The promoter sequence contains transcriptional control sequences that mediate the expression of the polypeptide. The leader sequence (or five prime untranslated region) of the present invention begins at the start site for transcription at the +1 position and ends just before the start codon (usually AUG) of the coding region. Thus it will be downstream to the mRNA initiation site and upstream of the structural gene encoding a polypeptide. It usually contains a ribosome binding site. The choice of leader sequence will as mentioned above affect the expression level of the downstream gene. Previously the preferred leader sequences for optimal expression in filamentous fungi have been obtained from the genes for *Aspergillus oryzae* TAKA amylase and *Aspergillus nidulans* triose phosphate isomerase.

In a preferred aspect, the nucleotide sequence of the invention comprises or consists of SEQ ID NO: 1 or SEQ ID NO: 2.

The present invention also relates to isolated polynucleotides comprising or consisting of nucleotide sequences having a degree of sequence identity to SEQ ID NO: 1 of at least 60%, preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have leader sequence functionality.

Modifications of a nucleotide sequence presented as SEQ ID NO: 1, e.g., a subsequence thereof, and/or by introduction of one or several nucleotide substitutions, may be possible without significantly affecting the functionality. SEQ ID NO: 2 represents such a modification since it is another variant of the same leader sequence isolated from another strain of the same species *A. niger*.

The present invention also relates to isolated polynucleotides obtained by (a) hybridizing a population of DNA under very low, low, medium, medium-high, high, or very high stringency conditions with the nucleotide sequence of SEQ ID NO: 1 or SEQ ID NO:2.

Nucleic Acid Constructs

The present invention also relates to nucleic acid constructs comprising an isolated polynucleotide of the present invention operably linked to a coding sequence and one or more (several) control sequences that direct the expression of the coding sequence in a suitable host cell under conditions compatible with the control sequences.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase. Most of these promoters will naturally be associated with an untranslated leader sequence positioned between the promoter and the gene it controls. It is envisaged that this leader sequence is replaced by the leader sequence of the invention.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

The control sequence may also be a polyadenylation sequence; a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that encodes a signal peptide linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of origins of replication useful in a filamentous fungal cell are AMA1 and ANSI (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a nucleic acid construct comprising the polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention operably linked to a coding sequence and one or more (several) control sequences. A construct or vector comprising a polynucleotide of the present invention is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, *Soc. App. Bacteriol. Symposium Series* No. 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a polypeptide of interest, comprising: (a) cultivating the recombinant host cell comprising a nucleic acid construct of the invention under conditions conducive for production of the polypeptide; and (b) recovering the polypeptide. In a preferred aspect, the cell is of the genus *Aspergillus, Fusarium* or *Trichoderma*. In a more preferred aspect, the cell is *Aspergillus niger, Aspergillus oryzae, Fusarium graminearum* or *Trichoderma reesei*. In a most preferred aspect, the cell is *Aspergillus niger*.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides produced using the polynucleotides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989) to obtain substantially pure polypeptides.

The present invention is further described by the following examples that should not be construed as limiting the scope of the invention.

EXAMPLES

Materials and Methods

Methods

Molecular cloning techniques are described in Sambrook, J., Fritsch, E. F., Maniatis, T. (1989) Molecular cloning: a laboratory manual (2nd edn.) Cold Spring Harbor Laboratory, Cold Spring Harbor, N.Y.

Enzymes

Enzymes for DNA manipulations (e.g. restriction endonucleases, ligases etc.) are obtainable from New England Biolabs, Inc. and were used according to the manufacturer's instructions.

Media and Reagents

Chemicals used for buffers and substrates were commercial products of analytical grade.

Cove-N(tf) plates are composed of 342.3 g of sucrose, 20 ml of Cove salt solution, 3 g of $NaNO_3$, and 30 g of noble agar, water to 1 liter.

Cove-N plates are composed of 30 g of sucrose, 20 ml of Cove salt solution, 3 g of $NaNO_3$, and 30 g of noble agar, water to 1 liter.

COVE salt solution is composed of 26 g KCl, 26 g $MgSO_4.7H_2O$, 76 g $KH_2PO_4$ and 50 ml Cove trace metals, water to 1 liter.

Trace metal solution for COVE is composed of 0.04 g $NaB_4O_7.10H_2O$, 0.4 g of $CuSO_4.5H_2O$, 1.2 g of $FeSO_4.7H_2O$, 1.0 g of $MnSO_4.H2O$, 0.8 g of Neutral amylase II $MoO_2.2H_2O$, and 10.0 g of $ZnSO_4.7H2O$, water to 1 liter.

Cove-N top agarose is composed of 342.3 g of Sucrose, 20 ml of COVE salt solution, 3 g of $NaNO_3$, and 10 g of low melt agarose, water to 1 liter.

Amyloglycosidase trace metal solution is composed of 6.8 g $ZnCl_2.7H_2O$, 2.5 g $CuSO_4.5H_2O$, 0.24 g $NiCl_2.6H_2O$, 13.9 g $FeSO_4.7H_2O$, 13.5 g $MnSO_4.H_2O$ and 3 g citric acid, water to 1 liter.

YPG is composed of 4 g of yeast extract, 1 g of $KH_2PO_4$, 0.5 g of $MgSO_4.7H_2O$ and 15 g of Glucose (pH 6.0), water to 1 liter.

STC buffer is composed of 0.8 M of sorbitol, 25 mM of Tris (pH 8), and 25 mM of $CaCl_2$, water to 1 liter.

STPC buffer is composed of 40% PEG4000 in STC buffer.

MLC is composed of 40 g Glucose, 50 g Soybean powder, 4 g/Citric acid (pH 5.0), water to 1 liter.

MSS is composed of 70 g Sucrose, 100 g Soybean powder (pH 6.0), water to 1 liter.

MU-1 is composed 260 g of Maltodextrin, 3 g of $MgSO_4.7H_2O$, 5 g of $KH_2PO_4$, 6 g of $K_2SO_4$, amyloglycosidase trace metal solution 0.5 ml and urea 2 g (pH 4.5), water to 1 liter.

Purchased Material (E. coli, Plasmid and Kits)

E. coli DH5-alpha (Toyobo) is used for plasmid construction and amplification. The commercial plasmids/vectors TOPO cloning kit (Invitrogen) and pBlue script II SK- (Stratagene #212206). are used for cloning of PCR fragments. Amplified plasmids are recovered with Qiagen® Plasmid Kit (Qiagen). Ligation is done with DNA ligation kit (Takara) or T4 DNA ligase (Boehringer Mannheim). Polymerase Chain Reaction (PCR) is carried out with Expand™ PCR system (Boehringer Mannheim). QIAquick™ Gel Extraction Kit (Qiagen) is used for the purification of PCR fragments and extraction of DNA fragment from agarose gel.

Strains

Aspergillus nidulans strain NRRL 1092 was used as donor of xylanase gene promoter and nitrate reductase gene terminator.

The expression host strain Aspergillus niger QMJi016-14-1 was isolated by Novozymes and is a derivative of Aspergillus niger NN049184 which was isolated from soil. QMJi016-14-1 is genetically modified to disrupt expression of ku70, oah and pyrG.

The expression host strain Aspergillus niger NN059180 (pyrG-) was isolated by Novozymes and is a derivative of Aspergillus niger NN049184 which was isolated from soil. NN059180 is genetically modified to disrupt expression of amyloglycosidase activities. Neutral amylase I gene in Aspergillus niger NN059180 is interrupted with E. coli Hygromicin B phosphontrasferase gene.

Aspergillus oryzae Bech2 is described in WO 00/39322 example 1.

Aspergillus oryzae strain #13-1 described in WO2006069289 is isolated by Novozymes.

Plasmids

The expression cassette plasmid pJaL790 is described in patent publication WO2005070962.

The expression cassette plasmid pHUda440 is described in patent publication WO2006/069289.

The expression cassette plasmid pCBPhycutiprepro is described in patent publication WO2008/017646.

pJaL574 is described in example 9 in WO07045248

Transformation of Aspergillus niger

Transformation of Aspergillus species can be achieved using the general methods for yeast transformation. The preferred procedure for the invention is described below.

Aspergillus niger host strain was inoculated to 100 ml of YPG medium supplemented with 10 mM uridine and incubated for 16 hrs at 32° C. at 80 rpm. Pellets were collected and washed with 0.6 M KCl, and resuspended 20 ml 0.6 M KCl containing a commercial β-glucanase product (GLUCANEX™, Novozymes NS, Bagsvrd, Denmark) at a final concentration of 20 mg per ml. The suspension was incubated at 32° C. at 80 rpm until protoplasts were formed, and then washed twice with STC buffer. The protoplasts were counted with a hematometer and resuspended and adjusted in an 8:2:0.1 solution of STC:STPC:DMSO to a final concentration of $2.5 \times 10^7$ protoplasts/ml. Approximately 4 μg of plasmid DNA was added to 100 μl of the protoplast suspension, mixed gently, and incubated on ice for 30 minutes. One ml of SPTC was added and the protoplast suspension was incubated for 20 minutes at 37° C. After the addition of 10 ml of 50° C. Cove-N top agarose, the reaction was poured onto Cove-N(tf) agar plates and the plates were incubated at 32° C. for 5 days.

| PCR amplification | |
|---|---|
| 5x PCR buffer (incl. $MgCl_2$) | 20 μl |
| 2.5 mM dNTP mix | 10 μl |
| Forward primer (100 μM) | 1 μl |
| Reverse primer (100 μM) | 1 μl |
| Expand High Fidelity polymerase (Roche) | 1 μl |
| Template DNA | 1 μl |
| Distilled water to | 100 μl |

| PCR conditions | | |
|---|---|---|
| 94° C. | 2 min | 1 cycle |
| 92° C. | 1 min | |
| 55° C. | 1 min | 30 cycles |
| 72° C. | 1-2 min | |
| 72° C. | 7 min | 1 cycle |

SF Cultivation for Glucoamylase Production

Spores of the selected transformants were inoculated in 100 ml of MLC media and cultivated at 30° C. for 2 days. 10 ml of MLC was inoculated to 100 ml of MU-1 medium and cultivated at 30° C. for 7 days. The supernatant was obtained by centrifugation.

SF Cultivation for Phytase Production

Spores of the selected transformants were inoculated in 100 ml of MSS media and cultivated at 30° C. for 2 days. 10 ml of MSS was inoculated to 100 ml of MU-1 medium and cultivated at 32° C. for 3 days. The supernatant was obtained by centrifugation.

Southern Hybridization

Mycelia of the selected transformants were harvested from overnight culture in 100 ml YPG medium, rinsed with distilled water, dried and frozen at −80° C. Ground mycelia were incubated with Proteinase K and RNaseA at 65° C. for 1 hrs. Genome DNA was recovered by phenol/CHCl3 extraction twice followed by EtOH precipitation and resuspended with distilled water.

Non-radioactive probes were synthesized using a PCR DIG probe synthesis kit (Roche Applied Science, Indianapolis Ind.) followed by manufacture's instruction. DIG labeled probes were gel purified using a QIAquick™ Gel Extraction Kit (QIAGEN Inc., Valencia, Calif.) according to the manufacturer's instructions.

Five micrograms of genome DNA was digested with appropriate restriction enzymes completely for 16 hours (40 µl total volume, 4 U enzyme/µl DNA) and run on a 0.8% agarose gel. The DNA was fragmented in the gel by treating with 0.2 M HCl, denatured (0.5M NaOH, 1.5M NaCl) and neutralized (1M Tris, pH7.5; 1.5M NaCl) for subsequent transfer in 20×SSC to Hybond N+ membrane (Amersham). The DNA was UV cross-linked to the membrane and pre-hybridized for 1 hour at 42° C. in 20 ml DIG Easy Hyb (Roche Diagnostics Corporation, Mannheim, Germany). The denatured probe was added directly to the DIG Easy Hyb buffer and an overnight hybridization at 42° C. was done. Following the post hybridization washes (twice in 2×SSC, room temperature, 5 min and twice in 0.1×SSC, 68° C., 15 min. each), chemiluminescent detection using the DIG detection system and CPD-Star (Roche) was done followed by manufacture's protocol. The DIG-labeled DNA Molecular Weight Marker II (Roche) was used for the standard marker.

Phytase Assay

1 FYT-V is the amount of enzyme which releases 1 µmol inorganic phosphate per minute under the standard conditions below.

| Reaction conditions | |
|---|---|
| pH | 5.5 |
| Temperature | 37° C. |
| Substrate concentration | 5.0 mM |
| Wavelength | 405 nm |
| Incubation time | 15 min |

75 µl/well enzyme solution (diluted in 0.25M sodium acetate, 0.005% Tween-20, pH5.5) is dispensed in a 96-well microtiter plates, then 75 µl substrate (Sodium phytate from rice (Aldrich 274321; MW 923.8) 10 mg/ml in 0.25 M Na-acetate buffer pH 5.5) is added and the plate is incubated for 15 min at 37° C. The reaction was stopped by adding 75 µl stop reagent (2.5% Ammonium hepta-morybdate and 0.06% ammonium vanadate in 10.9% nitric acid). Absorbance at 405 nm is measured on 100 µl samples in 96 well microtiter plates.

Glucoamylase Activity

Glucoamylase activity is measured in AmyloGlucosidase Units (AGU). The AGU is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

Amyloglycosidase Incubation:

| | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

Color Reaction:

| | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

Example 1

Expression of *Citrobacter* Phytase Controlled by Neutral Amylase II Promoter Combined with Different 5' Untranslated Region Sequence in *Aspergillus niger*

Construction of pHUda666

The following primers TCGA-F and TCGA-R which introduce a BamHI and an XhoI site, respectively, were designed to isolate cDNA of TC glucoamylase based on the nucleotide sequences information in the WO2006069289.

TCGA-F:
(SEQ ID NO: 3)
tggggatccaccatgcgtttcacgctcct

TCGA-R:
(SEQ ID NO: 4)
ctcgagttaattaactaccgccaggtgtcgttc

A PCR reaction with the cDNA of the *Aspergillus oryzae* strain #13-1 (disclosed in WO2006069289) as template was performed using a primer pair of TCGA-F and TCGA-R. The reaction products were isolated on a 1.0% agarose gel and 1.7 kb product band was excised from the gel. The 1.7 kb amplified DNA fragment was digested with BamHI and XhoI, and ligated into the *Aspergillus* expression cassette pJaL790 digested with BamHI and XhoI.

Cloning of *Aspergillus nidulans* pyrG Gene with Terminator Repeats

The following primers nidP-f and nidP-r which introduce NheI/SpeI and XbaI/SphI sites, respectively, were designed to amplify *Aspergillus nidulans* pyrG gene based on the nucleotide sequences information in the genome database of *Aspergillus nidulans*.

```
nidP-f:
                                      (SEQ ID NO: 5)
tttgctagcactagttactaaatgacgtttgtgaac nidP-r:
                                      (SEQ ID NO: 6)
ttgcatgctctagaggagcgaaccaattctc
```

A PCR reaction with the genome DNA of the *Aspergillus nidulans* NRRL1092 as template was performed with a primer pair, nidP-F and nidP-R. The reaction products were isolated on a 1.0% agarose gel and 1.8 kb product band was excised from the gel.

The 1.8 kb amplified DNA fragment was ligated using TOPO cloning kit (Invitrogen) followed by the manufacture's protocol. The ligation mixture was transformed into *E. coli* DH5α to create the plasmid pHUda795.

The following primers nidPT-f and nidPT-r which introduce a SpeI and an XbaI site, respectively, were designed to amplify *Aspergillus nidulans* pyrG terminator region based on the nucleotide sequences information in the genome database of *Aspergillus nidulans*.

```
nidPT-f:
                                      (SEQ ID NO: 7)
tttactagtacgagaaaagagttggact nidPT-r:
                                      (SEQ ID NO: 8)
tttctagagcgaaccaattctctcccagc
```

A PCR reaction with the genome DNA of the *Aspergillus nidulans* NRRL1092 as template was performed with a primer pair of nidPT-f and nidPT-r. The reaction products were isolated on a 1.0% agarose gel and the 0.3 kb product band was excised from the gel. The 0.3 kb amplified DNA fragment was digested with SpeI and XbaI, and ligated into the pHUda795 digested with SpeI. The ligation mixture was transformed into *E. coli* DH5α to create the expression plasmid pHUda797.

Construction of pTrapyrG

The 2.1 kb DNA fragment containing *Aspergillus nidulans* pyrG gene with its terminator repeats was recovered from pHUda797 by NheI and SphI digestion. The recovered 2.1 kb fragment was ligated to XbaI and SphI digested pHUda666. The ligation mixture was transformed into *E. coli* DH5☐ to create the expression plasmid pTrapyrG. Plasmid pTrapyrG comprised an expression cassette of TC glucoamylase based on the three copies of *Aspergillus niger* neutral amylase II promoter put in the same direction, *Aspergillus nidulans* triose phosphate isomerase non translated 5′ untranslated region sequence fused to the last *Aspergillus niger* neutral amylase II promoter (triple NA2/tpi promoter) and the *Aspergillus niger* amyloglycosidase terminator (AMG terminator), the selective marker pyrG with its terminator repeats from *Aspergillus nidulans*.

Construction of pTK

The 2.5 kb DNA fragment containing herpes simplex virus (HSV) thymidine kinase gene (TK) was recovered from pJaL574 by HindIII and SpeI digestion. The recovered 2.5 kb fragment was ligated to HindIII and SpeI digested pBlue script II SK-. The ligation mixture was transformed into *E. coli* DH5α to create the expression plasmid pTK.

Construction of pTK-5NA1

The following primers 5NA1F and 5NA1R which introduce a PmeI and NheI/SpeI sites, respectively, were designed to amplify *Aspergillus niger* 5′ flanking region of neutral amylase I (NAI) gene based on the nucleotide sequences information in the genome database of *Aspergillus niger*.

```
5NA1F:
                                      (SEQ ID NO: 9)
gtttaaacctatctgttccctccccccc 5NA1R:
                                      (SEQ ID NO: 10)
tttactagtgctagctgacttctatataaaaatgagta
```

A PCR reaction with the genome DNA of the *Aspergillus niger* NN059180 as template was performed with a primer pair of 5NA1F and 5NA1R. The reaction products were isolated on a 1.0% agarose gel and 1.8 kb product band was excised from the gel. The 1.8 kb amplified DNA fragment was digested with PmeI and NheI, and ligated to PmeI and SpeI digested pTK. The ligation mixture was transformed into *E. coli* DH5α to create the plasmid pTK-5NA1.

Construction of pTK-5NA1-3NA1

The following primers 3NA1F and 3NA1R which introduce an XbaI and a NotI site, respectively, were designed to amplify *Aspergillus niger* 3′ flanking region of neutral amylase I (NAI) gene based on the nucleotide sequences information in the genome database of *Aspergillus niger*.

```
3NA1F:
                                      (SEQ ID NO: 11)
tttctagagtatatgatggtactgctattc 3NA1R:
                                      (SEQ ID NO: 12)
gcggccgcgcattctcctagttactgatgact
```

A PCR reaction with the genome DNA of the *Aspergillus niger* NN059180 as template was performed with a primer pair of 3NA1F and 3NA1R. The reaction products were isolated on a 1.0% agarose gel and 1.4 kb product band was excised from the gel The 1.4 kb amplified DNA fragment was digested with XbaI and NotI, and ligated to XbaI and NotI digested pTK-5NA1. The ligation mixture was transformed into *E. coli* DH5α to create the plasmid pTK-5NA1-3NA1.

Construction of pIH142

The 6.2 kb DNA fragment containing TC glucoamylase expression cassette and pyrG with its terminator repeats from *Aspergillus nidulans* was recovered from pTrapyrG by NheI and XbaI. The recovered 6.2 kb fragment was ligated to XbaI digested pTK-5NA1-3NA1. The ligation mixture was transformed into *E. coli* DH5α to create the expression plasmid pIH142.

Construction of prika156

A part of the synthetic *Citrobacter* phytase fused with *Humicola* Cutinase signal sequence was amplified with primer pairs, p384 and p387 or p385 and p386, using pCBPhy-cutiprepro as template. Both obtained PCR fragments were recovered from agarose gel. Then, using the PCR fragments amplified with p384 and p387, and p385 and p386, SOE-PCR (splicing by overlap extension PCR) was carried out with a primer pair of p384 and p386. The obtained PCR flagment containing signal+pro+Citrobactor phytase was recovered from agarose gel and digested with NheI and PacI. The recovered 1.3 kb fragment was ligated to NheI and PacI digested pIH142. The ligation mixture was transformed into *E. coli* DH5α to create the expression plasmid prika156.

p384
(SEQ ID NO: 13)
aagtcagctagccgtcggtgtgatggaaatcc p385
(SEQ ID NO: 14)
tcaaaattgaggatttagtcttgatcggatctccaccatgaagttctt p386
(SEQ ID NO: 15)
acccggatcttaattaactactctgtgac p387
(SEQ ID NO: 16)
aagaacttcatggtggagatccgatcaagactaaatcctcaattttga Construction of prika161

The *Aspergillus niger* neutral amylase II promoter without its 5' untranslated region combined with 5' untranslated region of putative alkyl sulatase gene from *Aspergillus niger* CBS 513.88 SEQ ID NO: 1 was amplified by PCR using primers p264 and p310.

p264
(SEQ ID NO: 17)
ttcgctagcatggtgttttgatc p310
(SEQ ID NO: 18)
tggtggatccgatcaagactaaatcctcaattttgaagaatttgtgtt
gtctgagttcagactcgagatgaattgatattggtgttctgagattgt
tgctccaagcatggcatccctt The sequence of 5' untranslated region of putative alkyl sulfatase gene was designed based on the sequence information of *Aspergillus niger* CBS 513.88 and the sequence is shown in SEQ ID NO: 1.

The obtained 0.6 kb PCR fragment of *Aspergillus niger* neutral amylase II promoter without its 5'untranslated region combined with 5' untranslated region of putative alkyl sulfatase gene was recovered from agarose gel and digested with NheI and BamHI, and ligated into prika156 digested with BglII and NheI. The ligation mixture was transformed into *E. coli* DH5α to create the expression plasmid prika161. prika161 comprised an expression cassette of *Citrobacter* phytase based on the *Aspergillus niger* neutral amylase II promoter, *Aspergillus niger* 5' untranslated region of putative alkyl sulfatase gene fused to the *Aspergillus niger* neutral amylase II promoter (NA2/pas promoter) and the *Aspergillus niger* amyloglycosidase terminator (AMG terminator), the selective marker pyrG with its terminator repeats from *Aspergillus nidulans*, simplex virus (HSV) thymidine kinase gene between *Aspergillus nidulans* grycerol phosphate dehydrogenase (gpd) promoter and terminator of trpC gene involved in tryptophan biosynthesis, 5' and 3' flanking region of *Aspergillus niger* neutral amylase I.

Construction of prika162

The *Aspergillus niger* neutral amylase II promoter without its 5' untranslated region combined with 5' untranslated region of *Aspergillus nidulans* triose phosphate isomerase was amplified by PCR using primers p264 and p310.

p262
(SEQ ID NO: 19)
tcggctagcatggtgttttgatcatttt p263
(SEQ ID NO: 20)
cgggatcccccagttgtgtatatagagg The obtained 0.6 kb PCR fragment of *Aspergillus niger* neutral amylase II promoter without its 5' untranslated region combined with 5' untranslated region of *Aspergillus nidulans* triose phosphate isomerase was recovered from agarose gel and digested with NheI and BamHI, and ligated into prika156 digested with BglII and NheI. The ligation mixture was transformed into *E. coli* DH5α to create the expression plasmid prika162. prika162 comprised an expression cassette of *Citrobacter* phytase based on the *Aspergillus niger* neutral amylase II promoter, *Aspergillus nidulans* 5' untranslated region of triose phosphate isomerase fused to the *Aspergillus niger* neutral amylase II promoter (NA2/tpi promoter) and the *Aspergillus niger* amyloglycosidase terminator (AMG terminator), the selective marker pyrG with its terminator repeats from *Aspergillus nidulans*, simplex virus (HSV) thymidine kinase gene between *Aspergillus nidulans* grycerol phosphate dehydrogenase (gpd) promoter and terminator of trpC gene involved in tryptophan biosynthesis, 5' and 3' flanking region of *Aspergillus niger* neutral amylase I.

Construction of prika163

The *Aspergillus niger* neutral amylase II promoter without its 5' untranslated region combined with 5' untranslated region of putative alkyl sulfatase gene from JGI genome database having SEQ ID NO:2 was amplified by PCR using primers p264 and p310.

p264
(SEQ ID NO: 21)
ttcgctagcatggtgttttgatc p270
(SEQ ID NO: 22)
ggtggatccgatcaaaactaaatcctcaattctgaagggattttgttgtt
tgggttcagactcgagatgaattgatatcgctgttctgagattgttgctc
caagcatggcatccctt The sequence of 5' untranslated region of putative alkyl sulfatase gene was designed based on the sequence information of JGI genome database and is shown in SEQ ID NO: 2.

The obtained 0.6 kb PCR fragment of *Aspergillus niger* neutral amylase II promoter without its 5' untranslated region combined with 5' untranslated region of putative alkyl sulfatase gene was recovered from agarose gel and digested with NheI and BamHI, and ligated into prika156 digested with BglII and NheI. The ligation mixture was transformed into *E. coli* DH5α to create the expression plasmid prika163. prika163 comprised an expression cassette of *Citrobacter* phytase based on the *Aspergillus niger* neutral amylase II promoter, *Aspergillus niger* 5' untranslated region of putative alkyl sulfatase gene fused to the *Aspergillus niger* neutral amylase II promoter (NA2/pas-J promoter) and the *Aspergillus niger* amyloglycosidase terminator (AMG terminator), the selective marker pyrG with its terminator repeats from *Aspergillus nidulans*, simplex virus (HSV) thymidine kinase gene between *Aspergillus nidulans* grycerol phosphate dehydrogenase (gpd) promoter and terminator of trpC gene involved in tryptophan biosynthesis, 5' and 3' flanking region of *Aspergillus niger* neutral amylase I.

prika161, prika162 and prika163 were introduced into *Aspergillus niger* strain QMJi016-14-1. Transformants were selected from the Cove-N(tf) medium. Randomly selected transformants were inoculated onto Cove-N plates with 2.5 µM 5-Flouro-2-deoxyuridine (FdU), an agent which kills cells expressing the herpes simplex virus (HSV) thymidine kinase gene (TK) harbouring in prika161, prika162 and prika163. Strains which grew well on Cove-N plates with 2.5 µM FdU were purified and subjected to Southern blotting analysis to confirm whether the expression cassette in prika160, prika161 or prika162 was integrated at the defined loci correctly or not.

Genomic DNA extracted from 161-6, 11, 15 (transformants of prika161), 162-3, 5, 7 (transformant of prika162), and 163-5, 11, 12 (transformant of prika163) was digested by NcoI.

Non-radioactive probes were synthesized using the following set of primers to analyze the selected transformants. For 5' NA1 flanking region, forward primer: aatccggatcctttcctata (SEQ ID NO: 23), reverse primer: gatggagcgcgcctagaagc (SEQ ID NO: 24), for phytase gene from *Citrobacter*, forward primer: ttcaccaccatcctcagcac (SEQ ID NO: 25), reverse primer: tcttgacctgcaaagtgttg (SEQ ID NO: 26)

By the right integration event, a hybridized signal at the size of 2.9 kb by NcoI digestion was shifted to 4.4 kb probed with 5'NA1 flanking region and a 4.4 kb band was detected probed with the *Citrobacter* phytase probe. Among the strains given the right integration events, three strains from the each construct, 161-6, 11, 15, 162-3, 5, 7, and 163-5, 11, 12 were chosen. The phytase activities of the supernatants of each transformants were determined.

Table 1 shows average phytase activity of the selected transformants, relative to the average activity of the transformants of prika162.

TABLE 1

Expression results

| Strain | Plasmid | Promoter | 5' untranslated region | Phytase relative activities |
|---|---|---|---|---|
| 161-6, 11, 15 | prika161 | NA 2 | SEQ ID NO: 1 | 1.21 |
| 162-3, 5, 7 | prika162 | NA 2 | TPI | 1.00 |
| 163-5, 11, 12 | prika163 | NA 2 | SEQ ID NO: 2 | 1.09 |

Example 2

Expression of *Citrobacter* Phytase Controlled by Catalase Promoter Combined with 5'UTR of Putative Alkyl Sulfatase Gene Sequence in *Aspergillus niger*

Construction of prika157 and prika158 pHiTe8 (described in example 4) or prika150R (described in example 4) was digested by NheI and BamHI and the 1.0 kb region of *Aspergillus niger* catalase promoter in pHiTe8 or the 1.0 kb region of *Aspergillus niger* catalase promoter without its 5'untranslated region fused to 5' untranslated region of putative alkyl sulfatase gene (SEQ ID NO:1) in prika150R was recovered from agarose gel and ligated into prika156 digested with BglII and NheI. The ligation mixture was transformed into *E. coli* DH5α to create the expression plasmid prika157 and prika158. prika157 comprised an expression cassette of *Citrobacter* phytase based on the *Aspergillus niger* catalase promoter, *Aspergillus niger* 5' untranslated region of putative alkyl sulfatase gene (SEQ ID NO:1) fused to the *Aspergillus niger* catalase promoter and the *Aspergillus niger* amyloglycosidase terminator (AMG terminator), the selective marker pyrG with its terminator repeats from *Aspergillus nidulans*, simplex virus (HSV) thymidine kinase gene between *Aspergillus nidulans* grycerol phosphate dehydrogenase (gpd) promoter and terminator of trpC gene involved in tryptophan biosynthesis, 5' and 3' flanking region of *Aspergillus niger* neutral amylase I. prika158 was the same construct as prika157 except for harboring *Aspergillus niger* catalase promoter instead of *Aspergillus niger* catalase promoter and *Aspergillus niger* 5' untranslated region of putative alkyl sulfatase gene (SEQ ID NO: 1) fused to the *Aspergillus niger* catalase promoter in prika157.

prika157 and prika158 were introduced into *Aspergillus niger* strain QMJi016-14-1. Transformants were selected from the Cove-N(tf) medium. Randomly selected transformants were inoculated onto Cove-N plates with 2.5 µM 5-Flouro-2-deoxyuridine (FdU), an agent which kills cells expressing the herpes simplex virus (HSV) thymidine kinase gene (TK) harbouring in prika157 and prika158. Strains which grew well on Cove-N plates with 2.5 µM FdU were purified and subjected to Southern blotting analysis to confirm whether the expression cassette in prika157 and prika158 was integrated at the defined loci correctly or not.

The following set of primers was used to analyze the selected transformants. For 5' NA1 flanking region, forward primer: aatccggatcctttcctata (SEQ ID NO: 23), reverse primer: gatggagcgcgcctagaagc (SEQ ID NO: 24), for phytase gene from *Citrobacter*, forward primer: ttcaccaccatcctcagcac ttcaccaccatcctcagcac (SEQ ID NO: 25), reverse primer: tcttgacctgcaaagtgttg (SEQ ID NO: 26)

Genomic DNA extracted from 157-1, 2, 5 (transformant of prika157) and 158-14, 16, 18 (transformant of prika158) was digested by NcoI.

Non-radioactive probes were synthesized using the following set of primers to analyze the selected transformants. For 5' NA1 flanking region, forward primer: aatccggatcctttcctata (SEQ ID NO: 23), reverse primer: gatggagcgcgcctagaagc (SEQ ID NO: 24), for phytase gene from *Citrobacter*, forward primer: ttcaccaccatcctcagcac (SEQ ID NO: 25), reverse primer: tcttgacctgcaaagtgttg (SEQ ID NO: 26).

By the right integration event, a hybridized signal at the size of 2.9 kb by NcoI digestion was shifted to 4.4 kb probed with 5'NA1 flanking region and a 4.4 kb band was detected probed with the *Citrobacter* phytase probe. Among the strains given the right integration events, three strains from the each construct, 157-1, 2, 15 and 158-14, 16, 18 were chosen. The phytase activities of the supernatants of each transformants were determined.

Table 2 shows average phytse activity of the selected transformants, relative to the average activity of the transformants of prika158.

TABLE 2

Expression results

| Strain | Plasmid | Promoter | 5' untranslated region | Phytase relative activities |
|---|---|---|---|---|
| 157-1, 2, 15 | prika157 | Catalase | SEQ ID NO: 1 | 1.09 |
| 158-14, 16, 18 | prika158 | Catalase | Catalase | 1.00 |

Example 3

Expression of a Glucoamylase Controlled by Neutral Amylase II Promoter Combined with Different 5' Untranslated Region in *Aspergillus niger*

Construction of pHuda440+pyrG

The 1.2 kb DNA fragment containing *Aspergillus nidulans* pyrG gene promoter region and coding region was amplified with a primer pair, ppyrG F and ppyrG R by PCR, using pHI142 (described in example 1) as template.

```
ppyrG F
                                         (SEQ ID NO: 27)
acttctagaatagcgacaagccgaacggc ppyrG R
                                         (SEQ ID NO: 28)
taccgccaggtgtcagtcaccctcaaagtccaactcttttct
```

The 0.8 kb DNA fragment containing *Aspergillus niger* amyloglycosidase terminator region and FRT-F3 target site was amplified with a primer pair, pTamg F and pTamg R by PCR using pIH142 as template.

```
pTamg F
                                         (SEQ ID NO: 29)
agaaaagagttggactttgagggtgactgacacctggcggta pTamg R
                                         (SEQ ID NO: 30)
gcttgcatgcactagctagttgaagttcctatactatttgaagaatag
gaactcggaataggaacttcaacctagaggagagagttgaac
```

Both obtained PCR fragments were recovered from agarose gel, then using the PCR fragments of *Aspergillus niger* amyloglycosidase terminator region, SOE-PCR was carried out with a primer pair of ppyrG F and pTamg R.

The obtained 1.9 kb PCR fragment of pyrG promoter, pyrG gene coding region, *Aspergillus niger* amyloglycosidase terminator and FRT-F3 target site for FLP was recovered from agarose gel and digested with XbaI and SphI, and ligated into pHUda440 digested with XbaI and SphI. The ligation mixture was transformed into *E. coli* DH5α to create the expression plasmid pHuda440+pyrG.

Construction of pHUda440+pyrG+FLP

The 0.7 kb DNA fragment containing *Aspergillus niger* amyloglycosidase terminator was amplified with a primer pair, pTer F and pTer R by PCR, using pHI142 as template.

```
pTer F
                                         (SEQ ID NO: 31)
gtccaggttcaactctctccactagcaaagtattttcggtacgattt pTer R
                                         (SEQ ID NO: 32)
gcttgcatgcactagctagttgaagttcctatactatttgaagaatagg
aactcggaataggaacttcaacctagaggagagagttgaac
```

In order to clone the 0.5 kb terminator region of *Aspergillus oryzae* nitrate reductase (niaD) gene, PCR was carried out with a primer pair, pTer F and pTer R by PCR, using genome DNA of *Aspergillus oryzae* Bech2 as template.

```
pTniaD F
                                         (SEQ ID NO: 33)
agaaaagagttggactttgagggtgactgacacctggcggta pTniaD R
                                         (SEQ ID NO: 34)
ctcctacatcaaccgccgcatctgagtcgagattatccaagggaatgac
tt
```

Both obtained PCR fragments were recovered from agarose gel, then using the 0.7 kb fragments of *Aspergillus niger* amyloglycosidase terminator region and the 0.5 kb fragment of *Aspergillus oryzae* nitrate reductase terminator, SOE-PCR was carried out with a primer pair of pTer F and pTniaD R. The obtained 1.2 kb fragment containing *Aspergillus niger* terminator+*Aspergillus oryzae* nitrate reductase terminator was recovered from agarose gel and termed fragment1.

The synthetic gene of yeast 2u FLP recombinase gene was designed following codon usage for the *A. oryzae* alpha amylase. The coding region of 2u FLP recombinase gene was synthesized at DNA 2.0 (DNA 2.0 USA, 1430 O'Brain Drive, Suite E, Mento Park, Calif. 94025 USA). Using the plasmid pJaL1008-G0184 containing the 1.3 kb codon optimized yeast 2u FLP recombinase gene as template, PCR was carried out with a primer pair, pFLP F and pFLP R.

```
pFLP F
                                         (SEQ ID NO: 35)
taagtcattcccttggataatctcgactcagatgcggcggttgatgtag
ga pFLP R
                                         (SEQ ID NO: 36)
ccaacaacccaactgacaggggatcgatccaccatgcccagttcgat
atcct
```

In order to clone the 0.7 kb promoter region of *Aspergillus nidulans* xylanase (xlnA) gene, PCR was carried out with a primer pair, ppxy F and ppxy R, using genome DNA of *Aspergillus nidulans* NRRL 1092 as template.

```
ppxy F
                                         (SEQ ID NO: 37)
aggatatcgaactggggcatggtggatcgatcccctgtcagttgggttg
ttgg ppxy R
                                         (SEQ ID NO: 38)
ggatggatccggaagtgcgttgatcattat
```

Both the obtained PCR fragments were recovered from agarose gel, then using the PCR fragments of codon optimized yeast 2u FLP recombinase gene and the PCR fragment of promoter region of *Aspergillus nidulans* xylanase (xlnA) gene, SOE-PCR was carried out with a primer pair of pFLP F and ppxy R. The obtained 1.9 kb fragment containing codon optimized yeast 2u FLP recombinase gene+promoter region of *Aspergillus nidulans* xylanase (xlnA) gene was recovered from agarose gel and termed fragment 2.

Then using fragment 1 and fragment 2, SOE-PCR was carried out with a primer pair of pTer F and ppxy R. The obtained 3.1 kb fragment containing *Aspergillus niger* amyloglycosidase terminator+*Aspergillus oryzae* nitrate reductase terminator+synthetic yeast 2u FLP recombinase gene+ promoter region of Aspergillus nidulans xylanase (xlnA) gene was recovered from agarose gel and digested with XhoI and BamHI and ligated into pHUda440+pyrG digested with XhoI and BglII. The ligation mixture was transformed into E. coli DH5α to create the expression plasmid pHuda440+pyrG+FLP.

Construction of prika113

In order to introduce yeast FLP recombinase target site FRT upstream of NA2/tpi promoter, PCR was carried out with a primer pair of pFRT F and pFRT R, using pHuda440+pyrG+FLP as template.

pFRT F
(SEQ ID NO: 39)
tttttacgtaaatatcagccctaacgtaatcggtaagcgagttgcccgcg caagcgagttgcccaccacccgccatataaaaatttaaaatgatcaaaac accatgctagcgaagttcctatactttctagagaataggaactcggaata ggaacttcaagatgaattcgcggccgcggc pFRT R
(SEQ ID NO: 40)
gcaccatatgcggtgtgaaataccgcacag The obtained 0.4 kb fragment containing yeast FLP recombinase target site FRT and a part of Aspergillus niger neutral amylase II promoter was recovered from agarose gel and digested with NdeI and SnaBI and ligated into pHUda440+pyrG+FLP digested with NdeI and SnaBI. The ligation mixture was transformed into E. coli DH5α to create the expression plasmid prika113. prika113 comprised an expression cassette of TC glucoamylase based on the Aspergillus niger neutral amylase II promoter, 5' untranslated region of Aspergillus niger triose phosphate isomerase gene fused to the Aspergillus niger neutral amylase II promoter and the Aspergillus niger amyloglycosidase terminator (AMG terminator), synthetic yeast 2u FLP recombinase gene between promoter region of Aspergillus nidulans xylanase (xlnA) gene and Aspergillus oryzae nitrate reductase terminator, the selective marker pyrG from Aspergillus nidulans. All genes mentioned above are flanked by FRT-F and FRT-F3 target sequences of Saccharomyces cerevisiae 2u FLP recombinase on the both ends.

Construction of prika117 and prika133

Neutral amylase II promoter without its 5' untranslated region fused to 5' untranslated region of putative alkyl sulfatase gene (SEQ ID NO:2) or neutral amylase II promoter without its 5' untranslated region combined to 5' untranslated region of putative alkyl sulfatase gene (SEQ ID NO:1) was amplified with primer pairs, pNA2F and pb-pas (J)R, or pNA2F and pb-pas(D)R using prika113 as template. Both the obtained 0.6 kb DNA fragment containing neutral amylase II promoter without its 5' untranslated region fused to 5' untranslated region of putative alkyl sulfatase gene (SEQ ID NO:2), or neutral amylase II promoter without its 5' untranslated region combined to 5' untranslated region of putative alkyl sulfatase gene (SEQ ID NO: 1) was recovered from agarose gel, cut by NheI and BamHI, and introduced into prika113 digested with NheI and BamHI. Plasmid preparation was carried out in E. coli DH5α. Resulting plasmids were termed prika117 and prika133.

pNA2F
(SEQ ID NO: 41)
cttcgctagcatggtgttttgatcatttt pb-pas(J)R
(SEQ ID NO: 42)
tggtggatccgatcaaaactaaatcctcaattctgaagggattttgttg
tttgggttcagactcgagatgaattgatatcgctgttctgagattgttg
ctccaagcatggcatcccctt pb-pas(D)R
(SEQ ID NO: 43)
atggtggatccgatcaagactaaatcctcaattttgaagaatttgtgtt
gtctgagttcagactcgagatgaattgatattggtgttctgagattgtt
gctccaagcatggcatcccctt prika117 comprised an expression cassette of TC glucoamylase based on the Aspergillus niger neutral amylase II promoter, 5' untranslated region of putative alkyl sulfatase gene (SEQ ID NO: 2) fused to the Aspergillus niger neutral amylase II promoter (NA2/pas) and the Aspergillus niger amyloglycosidase terminator (AMG terminator), synthetic yeast 2u FLP recombinase gene between promoter region of Aspergillus nidulans xylanase (xlnA) gene and Aspergillus oryzae nitrate reductase terminator, the selective marker pyrG from Aspergillus nidulans. All genes mentioned above are flanked by FRT-F and FRT-F3 target sequences of Saccharomyces cerevisiae 2u FLP recombinase on the both ends. prika133 is the same construct as prika117 except for harboring Aspergillus niger 5' untranslated region of putative alkyl sulfatase gene (SEQ ID NO:1) instead of 5' untranslated region of putative alkyl sulfatase gene (SEQ ID NO: 2) in prika117.

prika113, prika117 and prika133 were introduced into Aspergillus niger NN059180. Transformants were selected from the Cove-N(tf) supplemented with 1% D-xylose medium.

Randomly selected transformants were inoculated onto Cove-N plates with 0.2 g/l Hygromycin B, an agent which kills cells NOT expressing the E. coli Hygromicin B phosphontrasferase gene located at NA1 locus of Aspergillus niger NN059180. Strains which could not grow on Cove-N plates with Hygromycin B were purified and subjected to Southern blotting analysis to confirm whether the expression cassette in prika113, prika117 and prika133 was integrated at the defined loci correctly or not.

Genomic DNA extracted from 113-2, 5 (transformants of prika113), 117-3, 4 (transformants of prika117), and 133-3, 7 (transformants of prika133), was digested by NcoI.

Non-radioactive probes were synthesized using the following set of primers to analyze the selected transformants. For 5' NA1 flanking region, forward primer: aatccggatcctttc-ctata (SEQ ID NO: 23), reverse primer: gatggagcgcgccta-gaagc (SEQ ID NO: 24), for glucoamylase gene, forward primer: tgattgcaagtccgagcaca (SEQ ID NO: 44), reverse primer: gaggtttgtccgatgcgatt (SEQ ID NO: 45)

By the right integration event, a hybridized signal at the size of 3.1 kb by NcoI digestion was shifted to 3.6 kb probed with 5'NA1 flanking region and a 3.6 kb band was detected probed with the glucoamylase probe. Among the strains given the right integration events, two strains from the each construct, 113-2, 5, 117-3, 4, and 133-3, 7 were chosen. The glucoamylase activities of the supernatants of each transformants were determined.

Table 3 shows average glucoamylase activity of the selected transformants, relative to the average activity of the transformants of prika113.

TABLE 3

Expression results

| Strain | Plasmid | Promoter | 5' untranslated region | Glucoamylase relative activities |
|---|---|---|---|---|
| 113-2, 5 | prika113 | NA 2 | TPI | 1.00 |
| 117-3, 4 | prika117 | NA 2 | SEQ ID NO: 2 | 1.32 |
| 133-3, 7 | prika133 | NA 2 | SEQ ID NO: 1 | 1.39 |

Example 4

Expression of a Glucoamylase Controlled by Catalase Promoter Combined with 5'Untranslated Region of Putative Alkyl Sulfatase Gene in *Aspergillus niger*

Construction of pHiTe8, prika150R and prika154

The 1.0 kb region of *Aspergillus niger* catalase promoter, *Aspergillus niger* catalase promoter without its 5' untranslated region fused to 5'untranslated region of putative alkyl sulfatase gene (SEQ ID NO:1) and *Aspergillus niger* catalase promoter without its 5' untranslated region fused to 5' untranslated region of putative alkyl sulfatase gene (SEQ ID NO: 2) was amplified by PCR with primer pairs, pHiTe08 F and pHiTe08 R, p354 and p355, or p354 and p361 using genome DNA of *Aspergillus niger* NN059180 as template.

pHiTe08 F
(SEQ ID NO: 46)
ctagctagccgtcggtgtgatggaaatc pHiTe08 R
(SEQ ID NO: 47)
cgcggatccgaagggaaggggggaagttg p354
(SEQ ID NO: 48)
ttcgctagccgtcggtgtgatgga p355
(SEQ ID NO: 49)
ggtggatccgatcaagactaaatcctcaattttgaagaatttgtgttgt
ctgagttcagactcgagatgaattgatattggtgttctgagattgttga
agatgaggcaattggagca p361
(SEQ ID NO: 50)
ggtggatccgatcaaaactaaatcctcaattctgaagggattttgttgt
ttgggttcagactcgagatgaattgatatcgctgttctgagattgttga
agatgaggcaattggagcag The obtained PCR containing *Aspergillus niger* catalase promoter, *Aspergillus niger* catalase promoter fused to 5'untranslated region of putative alkyl sulfatase gene (SEQ ID NO: 1) or *Aspergillus niger* catalase promoter fused to 5'untranslated region of putative alkyl sulfatase gene (SEQ ID NO: 2) was recovered from agarose gel and digested with NheI and BamHI, and ligated into prika113 digested with BglII and NheI. The ligation mixture was transformed into *E. coli* DH5α to create the expression plasmid pHiTe8, prika150R or prika154. pHiTe8 comprised an expression cassette of the glucoamylase based on the *Aspergillus niger* catalase promoter and the *Aspergillus niger* amyloglycosidase terminator (AMG terminator), codon optimized yeast 2u FLP recombinase gene between promoter region of *Aspergillus nidulans* xylanase (xlnA) gene and *Aspergillus oryzae* nitrate reductase terminator, the selective marker pyrG from *Aspergillus nidulans*. All genes mentioned above are flanked by FRT-F and FRT-F3 target sequences of *Saccharomyces cerevisiae* 2u FLP recombinase on the both ends. prika150R is the same construct as pHiTe8 except for harboring *Aspergillus niger* catalase promoter and 5' untranslated region of putative alkyl sulfatase gene (SEQ ID NO:1) fused to the *Aspergillus niger* catalase promoter instead of *Aspergillus niger* catalase promoter in pHiTe8. prika154 is the same construct as prika150R except for harboring 5' untranslated region of putative alkyl sulfatase gene (SEQ ID NO: 2) instead of 5' untranslated region of putative alkyl sulfatase gene (SEQ ID NO: 1).

The pHiTe8, prika150R and prika154 were introduced into *Aspergillus niger* NN059180. Transformants were selected from the Cove-N(tf) supplemented with 1% D-xylose medium. Randomly selected transformants were inoculated onto Cove-N plates with 0.2 g/L of Hygromycin B, an agent which kills cells NOT expressing the *E. coli* Hygromicin B phosphontrasferase gene located at NA1 locus of *Aspergillus niger* NN059180. Strains which could not grow on Cove-N plates with Hygromycin B were purified and subjected to Southern blotting analysis to confirm whether the expression cassette in pHiTe8, prika150R and prika154 were integrated at the defined loci correctly or not.

Genomic DNA extracted from 8-1, 6 (transformants of pHiTe8), 150-1, 9 (transformants of prika150R), and 154-1, 5 (transformants of prika154), was digested by NcoI.

The following set of primers was used to analyze the selected transformants. For 5' NA1 flanking region, forward primer: aatccggatcctttcctata (SEQ ID NO: 23), reverse primer: gatggagcgcgcctagaagc (SEQ ID NO: 24). For the glucoamylase gene, forward primer: tgattgcaagtccgagcaca (SEQ ID NO: 44), reverse primer: gaggtttgtccgatgcgatt (SEQ ID NO: 45).

By the right integration event, a hybridized signal at the size of 3.1 kb by NcoI digestion was shifted to 4.0 kb probed with 5'NA1 flanking region and a 4.0 kb band was detected probed with the glucoamylase probe. Among the strains given the right integration events, two strains from the each construct, pHiTe8, prika150R, and prika154 were chosen. The glucoamylase activities of the supernatants of each transformants were determined.

Table 4 shows average glucoamylase activity of the selected transformants, relative to the average activity of the transformants of pHiTe8.

TABLE 4

Expression results

| Strain | Plasmid | Promoter | 5' untranslated region | Glucoamylase relative activities |
|---|---|---|---|---|
| 8-1, 6 | pHiTe8 | Catalase | Catalase | 1.00 |
| 150-1, 9 | prika150R | Catalase | SEQ ID NOI: 1 | 1.82 |
| 154-1, 5 | prika154 | Catalase | SEQ ID NO: 2 | 1.57 |

What is claimed is:

1. A nucleic acid construct comprising at least one first nucleic acid sequence comprising a promoter upstream of a second nucleic acid sequence comprising a polynucleotide having leader sequence functionality operably linked to a third nucleic acid sequence encoding a polypeptide of interest and located downstream of the second nucleic acid sequence, wherein the leader sequence begins at the start site for transcription at the +1 position and ends just before the start codon of the coding region, wherein the polynucleotide having leader sequence functionality comprises SEQ ID NO: 1, wherein the polynucleotide having leader sequence functionality is foreign to the promoter comprised in the first nucleic acid sequence and foreign to the third nucleic acid sequence encoding the polypeptide of interest, and wherein the polynucleotide having leader sequence functionality improves recombinant production of the polypeptide of interest.

2. The nucleic acid construct of claim 1, wherein the promoter is selected from the group consisting of NA2, any promoter derived from an amylase gene, any promoter derived from a protease gene, any promoter derived from an oxidase gene, any promoter derived from a gene encoding a glycolytic enzyme, any promoter derived from a gene encoding a ribosomal or histone protein, or any promoter derived from a gene encoding a heat shock protein, an acetyl-CoA acetyl transferase, a translational elongation factor, a CipC-like antibiotic response protein, an invertase or an exo-inulinase.

3. The nucleic acid construct of claim 1, wherein the polynucleotide having leader sequence functionality consists of SEQ ID NO: 1.

4. The nucleic acid construct of claim 2, wherein
(a) the amylase gene is a glucoamylase gene, a neutral amylase gene, or an acid amylase gene,
(b) the protease gene is a pepA, pepB, pepC, pepD, or pepE gene,
(c) the oxidase gene is a superoxide dismutase gene, a catalase gene, or a mono-oxidase gene, and
(d) the gene encoding a glycolytic enzyme is an enolase gene, a glyceraldehyde-3-phosphate dehydrogenase gene, or a hexokinase gene.

5. A recombinant expression vector comprising the nucleic acid construct of claim 1.

6. A recombinant host cell comprising the nucleic acid construct of claim 1.

7. A method of producing a polypeptide of interest, comprising: (a) cultivating the recombinant host cell of claim 6 under conditions conducive for production of the polypeptide; and (b) recovering the polypeptide.

8. The method of claim 7, wherein the polypeptide is an enzyme.

9. The method of claim 8, wherein the enzyme is selected from the group consisting of proteases, amylases, glucoamylases, lipases, cellulases, phytases, oxidative enzymes, oxidoreductases and pectinases.

10. The method of claim 7, wherein the recombinant host cell is a filamentous fungus.

11. The method of claim 10, wherein the filamentous fungus is selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces,* (Original) *Thermoascus, Thielavia, Tolypocladium, Trametes* and *Trichoderma.*

12. The method of claim 11, wherein the *Aspergillus* is selected from the group consisting of *Aspergillus awamori, Aspergillus fumigatus, Aspergillus foetidus, Aspergillus japonicus, Aspergillus nidulans, Aspergillus niger* and *Aspergillus oryzae.*

13. The method of claim 12, wherein the *Aspergillus* is *Aspergillus niger.*

14. The method of claim 12, wherein the *Aspergillus* is *Aspergillus oryzae.*

* * * * *